United States Patent
Wada et al.

(10) Patent No.: US 9,853,223 B2
(45) Date of Patent: Dec. 26, 2017

(54) COMPOUND, ORGANIC PHOTOELECTRIC CONVERSION DEVICE AND SOLID-STATE IMAGING DEVICE

(71) Applicant: Kabushiki Kaisha Toshiba, Minato-ku (JP)

(72) Inventors: Atsushi Wada, Kawasaki (JP); Isao Takasu, Setagaya (JP); Honam Kwon, Kawasaki (JP); Satomi Taguchi, Ota (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 33 days.

(21) Appl. No.: 15/161,565

(22) Filed: May 23, 2016

(65) Prior Publication Data

US 2016/0351828 A1   Dec. 1, 2016

(30) Foreign Application Priority Data

May 28, 2015   (JP) .................................. 2015-108875

(51) Int. Cl.
*H01L 51/42*   (2006.01)
*H01L 51/00*   (2006.01)
*C07D 235/18*   (2006.01)

(52) U.S. Cl.
CPC ........ *H01L 51/0072* (2013.01); *C07D 235/18* (2013.01); *H01L 51/0052* (2013.01); *H01L 51/0058* (2013.01); *H01L 51/4253* (2013.01)

(58) Field of Classification Search
None
See application file for complete search history.

(56) References Cited

U.S. PATENT DOCUMENTS

| 6,878,469 B2 | 4/2005 | Yoon et al. |
| 2007/0063156 A1 | 3/2007 | Hayashi |

(Continued)

FOREIGN PATENT DOCUMENTS

| JP | 4308663 | 8/2009 |
| JP | 4677314 | 4/2011 |

(Continued)

*Primary Examiner* — Joseph Schoenholtz
(74) *Attorney, Agent, or Firm* — Oblon, McClelland, Maier & Neustadt, L.L.P.

(57) ABSTRACT

A compound of the embodiment includes the structure represented by the following general formula (1).

(1)

(Continued)

In the general formula (1), $R^1$ to $R^4$ respectively independently represent a hydrogen atom, a linear or branched alkyl group, a fluoroalkyl group, or an aryl group.

6 Claims, 11 Drawing Sheets

(56) References Cited

U.S. PATENT DOCUMENTS

2009/0223566 A1    9/2009    Mitsui et al.
2015/0179954 A1*   6/2015    Gessner ............... C07D 487/06
                                                        257/40

FOREIGN PATENT DOCUMENTS

| JP | 2011-119745 | 6/2011 |
| --- | --- | --- |
| WO | WO 03/060956 A2 | 7/2003 |
| WO | WO 03/060956 A3 | 7/2003 |

\* cited by examiner

COMPOUND, ORGANIC PHOTOELECTRIC CONVERSION DEVICE AND SOLID-STATE IMAGING DEVICE

CROSS-REFERENCE TO RELATED APPLICATION

This application is based upon and claims the benefit of priority from Japanese Patent Application No. 2015-108875, filed May 28, 2015, the entire contents of which are incorporated herein by reference.

FIELD

Embodiments of the present invention relate to a compound, an organic photoelectric conversion devise and a solid-state imaging device.

BACKGROUND

In an organic photoelectric conversion device, the research with the aim of the improvement of photoelectric conversion efficiency and the reduction of a dark current has been actively carried out by modifying hole-blocking materials. However, it might be impossible to sufficiently achieve the improvement of photoelectric conversion efficiency and the reduction of a dark current by using conventionally used materials.

DETAILED DESCRIPTION

Figure 1:
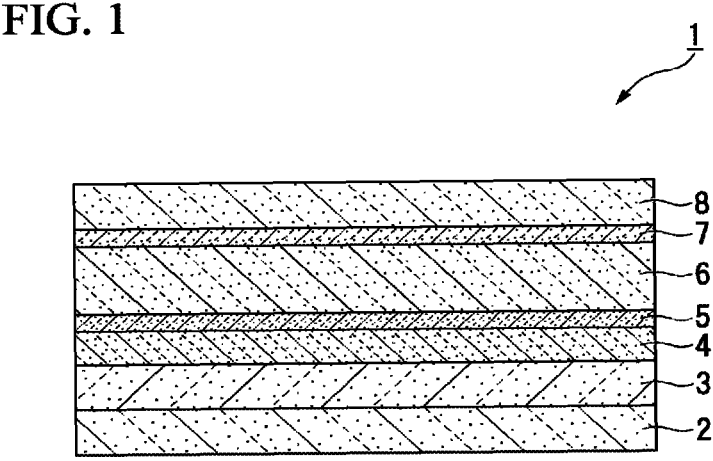
FIG. 1 is a schematic diagram representing the configuration of the organic photoelectric conversion devise of the embodiment.

Hereinafter, the compound, the organic photoelectric conversion devise and the solid-state imaging device according to the embodiments are described with reference to the drawings. In the drawings used in the following descriptions, the scale reductions of dimensions vary according to respective components in order to clarify components. Also, materials and dimensions exemplified in the following description are examples, and the embodiments are not necessarily limited to these and can be worked while appropriately modifying these.

First, the structure of the compound of the embodiment is described.

Examples of the compound of the embodiment include a compound represented by the following general formula (1).

[Chemical Formula 1]

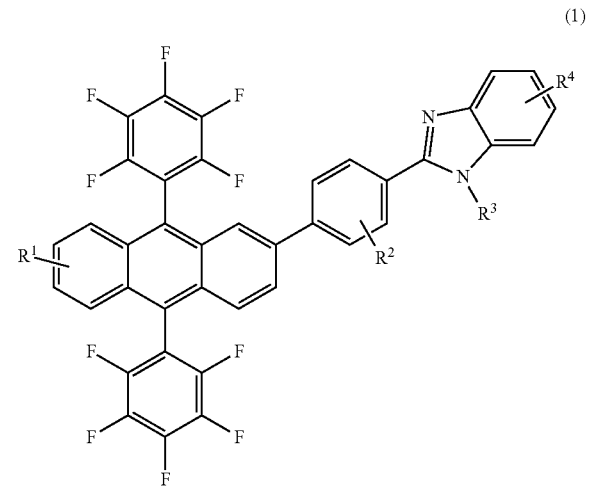

(1)

In the general formula (1), $R^1$ to $R^4$ respectively independently represent a hydrogen atom, a linear or branched alkyl group having 1 to 6 carbons, a fluoroalkyl group having 1 to 6 carbons, or an aryl group.

Herein, the substituent groups of $R^1$ to $R^4$ in the aformentioned general formula (1) can be selected appropriately according to the properties required for the compound.

For example, when deepening the HOMO level and the LUMO level of the compound, a trifluoromethyl group is selected as $R^1$ and $R^2$.

Also, for example, when increasing the thermal stability of the compound, a phenyl group is selected as $R^1$ and $R^2$.

Specific examples of the compound represented by the aforementioned general formula (1) include the compound represented by the following formula (2). Hereinafter, the compound represented by the following formula (2) is described as "F201".

[Chemical Formula 2]

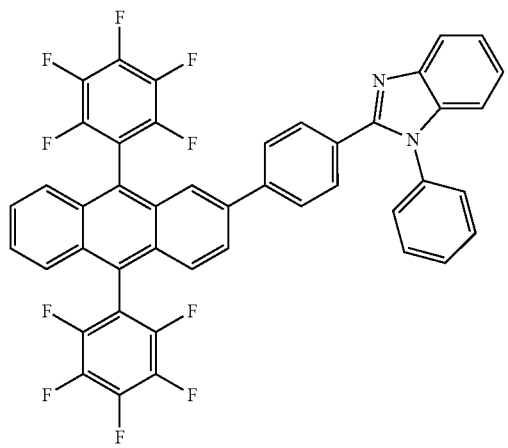

(2)

Because fluorine atoms are introduced in the compound represented by the aforementioned general formula (1) and the aforementioned formula (2), the HOMO (Highest Occupied Molecular Orbital) level and the LUMO (Lowest Unoccupied Molecular Orbital) level are deep. Therefore, by using the compound represented by the aforementioned general formula (1) or the aforementioned formula (2) as a hole-blocking layer, it is possible to provide an organic photoelectric conversion device and a solid-state imaging device having high photoelectric conversion efficiency and a low dark current.

Herein, the measurement of the HOMO level and the LUMO level can be carried out by the calculation using Gaussian (a DFT method in which B3LYP is used, and the basis function is 6-31G*), etc.

Next, the synthesis method for the compound of the embodiment is described.

First, under a nitrogen atmosphere, N-phenyl-O-phenylenediamine (NPOP) is dissolved in N-methylpyrrolidone (NMP). Thereafter, the NPOP solution is cooled, 4-bromobenzoyl chloride (4BC) is dissolved in NMP, and this 4BC solution is added dropwise in the NPOP solution. Thereafter, the reaction solution is stirred at room temperature for 1 hour to several hours. Thereafter, water is added dropwise therein, to thereby terminate the reaction, and the reaction solution is extracted with ethyl acetate. Thereafter, an organic layer is washed with a saturated saline solution, and is dried over anhydrous sodium sulfate. Thereafter, an organic layer is concentrated under a reduced pressure, to thereby obtain the compound represented by the following formula (3).

[Chemical Formula 3]

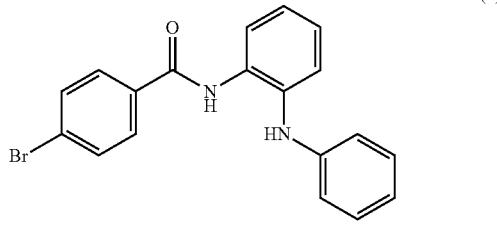

(3)

Next, under a nitrogen atmosphere, xylene is added to the compound represented by the formula (3) and p-toluene sulfonic acid, and the reaction solution is heated and refluxed to be dehydrated for several hours. Thereafter, the reaction solution is cooled to room temperature, and is filtrated to obtain the solid product. This solid product is dissolved again in chloroform, and the chloroform solution is washed with a saturated sodium bicarbonate aqueous solution and water. On the other hand, ethyl acetate is added to the xylene-soluble part which is the filtrate obtained by the filtration, and then, this mixed solution is washed with a saturated sodium bicarbonate aqueous solution and water in the same manner as described above. Thereafter, the organic layers are mixed, and the mixed solution is dried over anhydrous sodium sulfate. Thereafter, the mixed solution is concentrated under a reduced pressure, to thereby obtain a crude product. This crude product is purified through column purification, to thereby obtain the compound represented by the following formula (4).

[Chemical Formula 4]

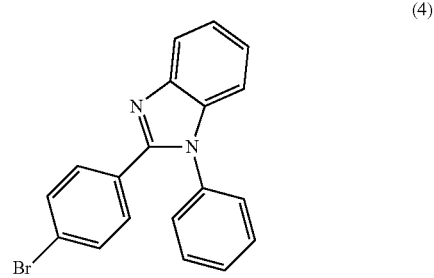

(4)

Next, under a nitrogen atmosphere, magnesium, tetrahydrofuran (THF) and iodine are added in a reactor, and the compound represented by the following formula (5) is added dropwise therein. Thereafter, the reaction solution is stirred for 1 hour to several hours. Then, the compound represented by the following formula (6) is added therein, and the reaction solution is further stirred. Thereafter, hydrochloric acid is added dropwise therein, to thereby terminate the reaction, and the reaction solution is extracted with ethyl acetate. Thereafter, the extracted solution is washed with a saturated saline solution and water. Then, anhydrous magnesium sulfate is added therein, and the solution is stirred for 1 hour to several hours. Thereafter, the solution is filtrated, and the obtained filtrate is concentrated under a reduced pressure, to thereby obtain the compound represented by the following formula (7).

[Chemical Formula 5]

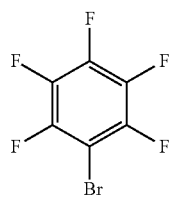

(5)

[Chemical Formula 6]

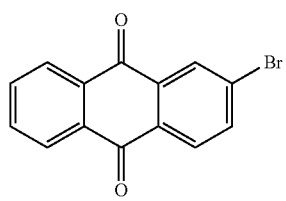

(6)

[Chemical Formula 7]

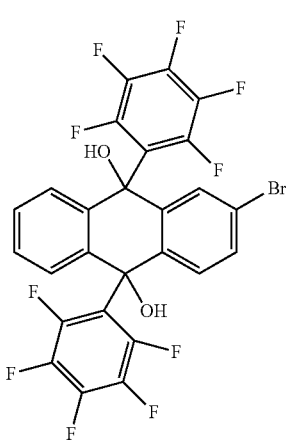

(7)

Next, the compound represented by the formula (7) is added and dissolved in the acetic acid. Thereafter, tin (II) chloride dihydrate is added therein and stirred for several hours. Thereafter, the reaction solution is cooled, and the reaction solution is added into water, followed by filtration to obtain the solid product. Thereafter, ethyl acetate is added to this solid so as to dissolve the solid product, and the obtained solution is washed with a saturated sodium bicarbonate aqueous solution and water. Thereafter, the anhydrous sodium sulfate is added therein, and the solution is stirred. One hour to several hours later, the solution is filtrated, and the obtained filtrate is concentrated under a reduced pressure, to thereby obtain the compound represented by the following formula (8).

[Chemical Formula 8]

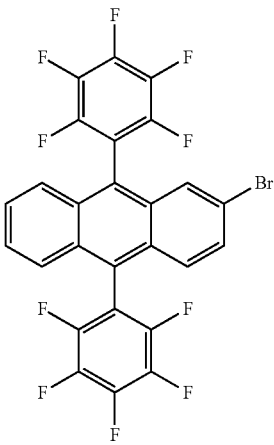

(8)

Next, under a nitrogen atmosphere, the compound represented by the formula (8) and the compound represented by the following formula (9) are added and dissolved in 1,4-dioxane. Thereafter, potassium acetate and [1,1'-bis(diphenylphosphino)ferrocene] dichloropalladium (II)-dichloromethane adduct (Pd(dppf)-CH$_2$Cl$_2$) are added therein, and the reaction solution is stirred for several hours. Thereafter, the reaction solution is cooled to room temperature and dispersed in water, and the precipitated solid product is collected by filtration. The obtained solid product is dissolved in chloroform, and anhydrous sodium sulfate and activated clay are added therein, followed by stirring. Thereafter, the solution is filtrated, and the obtained filtrate is concentrated under a reduced pressure, to thereby obtain the compound represented by the following formula (10).

[Chemical Formula 9]

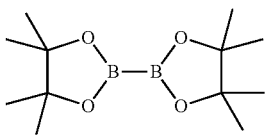

(9)

[Chemical Formula 10]

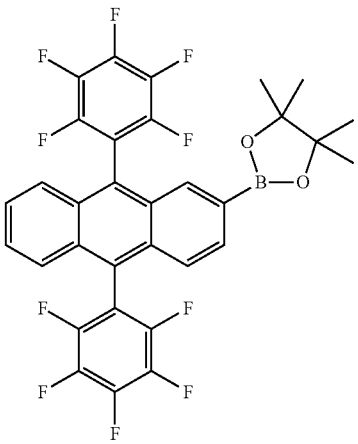

(10)

Next, under a nitrogen atmosphere, the compound represented by the formula (4) and the compound represented by the formula (10) are added and dissolved in xylene and 1,4-dioxane. Thereafter, a sodium carbonate aqueous solution and tetrakis(triphenylphosphine)palladium are added thereto, and the reaction solution is stirred. Thereafter, the reaction solution is cooled to room temperature, and chloroform is added therein. The reaction solution is separated into two layers, and the collected organic layer is washed with water. Thereafter, anhydrous sodium sulfate and activated clay are added in the organic layer, and the organic layer is stirred for 1 hour to several hours. Thereafter, the organic layer is filtrated, and xylene and chloroform are removed from the obtained filtrate by concentration under a reduced pressure, to thereby obtain a crude product. This crude product is purified by silica gel column chromatography, and the purified product is dried under a reduced pressure. Through these processes, it is possible to obtained F201 which is the target compound.

According to the embodiment described above, the compound contains the structure represented by the aforementioned general formula (1), and an organic photoelectric conversion device or a solid-state imaging device which includes this compound can achieve high photoelectric conversion efficiency and a low dark current.

Next, the organic photoelectric conversion device including the compound of the embodiment described above with reference to FIG. 1. FIG. 1 is a schematic diagram representing the configuration of the organic photoelectric conversion devise of the embodiment. As shown in FIG. 1, the organic photoelectric conversion device 1 includes the substrate 2, the anode 3, the planarization layer 4, the electron-blocking layer 5, the photoelectric conversion layer 6, the hole-blocking layer 7 and the cathode 8. Because of the organic photoelectric conversion device 1 of the embodiment, it is possible to absorb a light entering the organic photoelectric conversion device 1 and to perform photoelectrical conversion.

The substrate 2 is provided in order to support the other members. The material of the substrate 2 is not particularly limited as long as it is optically transmissive. Examples of this material include transparent substrates made of glass or a synthetic resin.

The thickness of the substrate 2 is not particularly limited as long as the strength of the substrate is enough to support the other member. Also, the shape, structure and size, etc. of the substrate 2 are not particularly limited, and can be appropriately selected depending on a use application and purpose, etc.

The anode 3 is laminated adjacent to the substrate 2. The anode 3 is electrically connected to the photoelectric conversion layer 6 described below, and receives the holes generated in the photoelectric conversion layer 6. The material of the anode 3 is not particularly limited as long as it is electroconductive. Examples of the material include an electroconductive metal oxide film, a semitransparent metal thin film and an organic electroconductive polymer.

Specific examples of a metal oxide film include a thin film of an indium oxide, a zinc oxide, a tin oxide, indium tin oxide (ITO) which is a complex of these, and a film (such as NESA) produced by using a conductive glass made of fluorine-doped tin oxide (FTO). Specific examples of a metal thin film include a thin film of gold, platinum, silver or copper. Specific examples of a conductive polymer include polyaniline and a derivative thereof, and polythiophene and a derivative thereof. Of these, it is preferable to use a transparent electrode made of ITO.

The thickness of the anode 3 is preferably within a range of 30 to 300 nm when using ITO. By setting the thickness of the anode 3 to 30 nm or more, it is possible to decrease the resistance of the anode 3 and to suppress a decrease in luminous efficiency due to an increase in the resistance. Also, by setting the thickness of the anode 3 to 300 nm or less, it is possible to maintain the flexibility of the anode 3 made of ITO and to prevent cracking thereof.

The anode 3 can be a single layer or can be formed by stacking layers made of materials having different work functions.

The planarization layer 4 is laminated adjacent to the opposite side of the substrate 2 at the anode 3. Because of the planarization layer 4, it is possible to relieve the unevenness of the anode 3. The material of the planarization layer 4 is not particularly limited as long as it can relieve the unevenness of the anode 3. Specific examples thereof include polythiophene-based polymers such as poly(ethylenedioxythiophene):poly(styrenesulfonic acid) mixture (PEDOT:PSS) which is a conductive ink.

The electron-blocking layer 5 is laminated between and adjacent to the planarization layer 4 and the photoelectric conversion layer 6 described below. The electron-blocking layer 5 prevents that the electrons are injected from the anode 3 into the side of the photoelectric conversion layer 6. Also, the electron-blocking layer 5 passes the holes generated in the photoelectric conversion layer 6 to the anode 3.

The material of the electron-blocking layer 5 is not particularly limited, and specific examples thereof include N,N'-bis(3-methylphenyl)-N,N'-diphenyl benzidine (IPD) and tris(4-carbazol-9-yl)phenylamine (TCTA).

The photoelectric conversion layer 6 is laminated between and adjacent to the electron-blocking layer 5 and the hole-blocking layer 7 described below. The photoelectric conversion layer 6 absorbs a light having entered the organic photoelectric conversion device 1 and performs photoelectric conversion, which generates electrons and holes.

The photoelectric conversion layer 6 can be comprised of a donor material and an acceptor material. The donor material is not particularly limited, and the specific examples thereof include coumarin, quinacridone and subphthalocyanine. The acceptor material is not particularly limited, and the specific examples thereof include fullerene (C60), perylene and phthalocyanine.

The hole-blocking layer 7 is laminated between and adjacent to the photoelectric conversion layer 6 and cathode 8 described below. The hole-blocking layer 7 prevents that the holes are injected from the cathode 8 onto the side of the photoelectric conversion layer 6. Also, the hole-blocking layer 7 passes the electrons generated in the photoelectric conversion layer 6 to the cathode 8.

Preferable examples of the material of the hole-blocking layer 7 include the compound represented by the aforementioned general formula (1) and F201 in terms of the improvement of photoelectric conversion efficiency and the suppression of a dark current.

The cathode 8 is laminated adjacent to the opposite side of the photoelectric conversion layer 6 at the hole-blocking layer 7. The cathode 8 is electrically connected to the photoelectric conversion layer 6 and receives the electrons generated in the photoelectric conversion layer 6. The material of the cathode 8 is not particularly limited as long as it is electroconductive. Specific examples thereof include a conductive metal oxide film, metal thin film and an alloy.

Specific examples of an alloy include a lithium-aluminum alloy, a lithium-magnesium alloy, a lithium-indium alloy, a magnesium-silver alloy, a magnesium-indium alloy, a magnesium-aluminum alloy, an indium-silver alloy, and a calcium-aluminum alloy.

The thickness of the cathode 8 is not particularly limited, but preferable examples of the thickness include a range of 10 to 150 nm. By setting the thickness to 10 nm or more, it is possible to decrease the resistance. Also, by setting the thickness to 150 nm or less, it is possible to reduce the time for the film formation and to prevent the adjacent layers from being damaged during the film formation.

The cathode 8 can be a single layer or can be formed by stacking layers made of materials having different work functions.

Next, a production method for the organic photoelectric conversion device 1 of the embodiment is described.

First, a glass substrate is prepared as a substrate 2. On the substrate 2, the transparent electroconductive film such as ITO is formed by a vacuum deposition method as the anode 3. Examples of the film formation method for the anode 3 other than the aforementioned vacuum deposition method include a sputtering method, an ion plating method, a plating method and a coating method.

Next, on the anode 3, a conductive ink such as PEDOT:PSS is applied by a method such as spin coating method as the planarization layer 4. Thereafter, the applied conductive ink is subjected to heating and drying by the hot plate, etc. so as to form a film. As the solution to be applied, it is possible to use a solution which is preliminarily filtrated by a filter.

Next, on the planarization layer 4, a film of a material such as TPD is formed by a vacuum deposition method as the electron-blocking layer 5. Examples of the film formation method for the electron-blocking layer 5 include a coating method in addition to the aforementioned vacuum deposition method.

Next, on the electron-blocking layer 5, a film of a material such as subphthalocyanine is formed by a vacuum deposition method as the photoelectric conversion layer 6. Examples of the film formation method for the photoelectric conversion layer 6 include a coating method in addition to the aforementioned vacuum deposition method.

Next, on the photoelectric conversion layer 6, a film of a material such as F201 is formed by a vacuum deposition method as the hole-blocking layer 7. Examples of the film formation method for the hole-blocking layer 7 include a coating method in addition to the aforementioned vacuum deposition method.

Next, on the hole-blocking layer 7, a film of a material such as aluminum is formed by a vacuum deposition method as the cathode 8. Examples of the film formation method for the cathode 8 include a sputtering method, an ion plating method, a plating method and a coating method in addition to the aforementioned vacuum deposition method.

Through the process described above, it is possible to produce the organic photoelectric conversion device 1 of the embodiment.

In the aforementioned embodiment, the substrate 2 is formed adjacent to the opposite side of the planarization layer 4 at the anode 3, but the substrate 2 can be formed adjacent to the opposite side of the hole-blocking layer 7 at the cathode 8.

Also, in the aforementioned embodiment, the organic photoelectric conversion device 1 includes the substrate 2, but can be free from substrate 2.

Also, in the aforementioned embodiment, the organic photoelectric conversion device 1 includes the planarization layer 4 and the electron-blocking layer 5, but can be free from one or both of the planarization layer 4 and the electron-blocking layer 5.

Also, in the aforementioned embodiment, the different materials are used for the anode 3 and the cathode 8, but the same material can be used for the anode 3 and the cathode 8. In this case, it is possible to use the aforementioned materials used for the anode 3 and the cathode 8. For example, both of the materials for the anode 3 and the cathode 8 can be ITO.

According to the embodiment described above, the organic photoelectric conversion device 1 includes the compound represented by the aforementioned general formula (1) or the aforementioned formula (2). Therefore, it is possible to achieve high photoelectric conversion efficiency and a low dark current.

Figure 2:
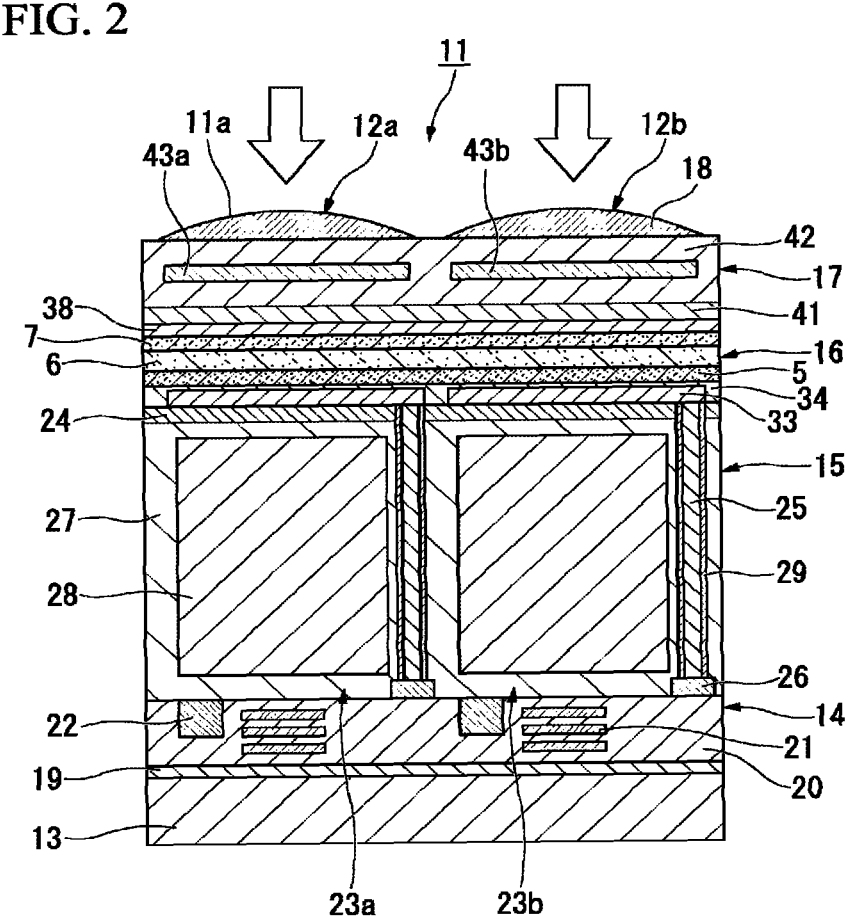
FIG. 2 is a schematic diagram representing the configuration of the solid-state imaging device of the embodiment.

Next, the solid-state imaging device 11 of the embodiment which includes the organic photoelectric conversion device t of the embodiment is described with reference to FIG. 2. FIG. 2 is a schematic diagram representing the configuration of the solid-state imaging device 11 of the embodiment. As shown in FIG. 2, the solid-state imaging device 11 is configured to include the adjacent pixels 12*a*, 12*b*.

Herein, only two pixels 12*a*, 12*b* are illustrated in the solid-state imaging device 11 shown in FIG. 2, but the solid-state imaging device 11 of the embodiment contains a plurality of pixels arranged in an array.

The solid-state imaging device 11 of the embodiment includes the supporting substrate 13, the wiring part 14, the 1st photoelectric conversion part 15, the 2nd photoelectric conversion part 16, the color filter part 17 and the microlens 18.

The solid-state imaging device 11 according to embodiment is a back side illumination typed photoelectric conversion device. Although a back side illumination typed photoelectric conversion device is illustrated in FIG. 2 as an example, the present invention is not limited thereto, and it is possible to use a front side illumination typed photoelectric conversion device.

The supporting substrate 13 is a substrate for supporting the wiring part 14. Examples of the supporting substrate 13 include a semiconductor substrate. Also, specific examples of the semiconductor substrate include a silicon (Si) substrate.

The wiring part 14 is provided on the side of the light receiving surface 11*a* of the supporting substrate 13. The wiring part 14 and the supporting substrate 13 are formed through the adhesive layer 19. The wiring part 14 includes the insulating layer 20, the multilayer wiring 21 and the read transistor 22.

The insulating layer 20 is provided between and adjacent to the adhesive layer 19 and the 1st photoelectric conversion part 15. Examples of the insulating layer 20 include a silicon oxide ($SiO_2$).

The multilayer wiring 21 is provided respectively at the pixels 12*a*, 12*b* in the insulating layer 20, and is connected to the read transistor 22, the storage diode 26 and the peripheral circuit (not illustrated).

The multilayer wiring 21 can output the charges stored in the photodiodes 23*a*, 23*b* and the storage diode 26 to the peripheral circuit (not illustrated) as an electric signal. The material of the multilayer wiring 21 is not particularly limited as long as it is an electroconductive material. Specific examples thereof include high melting point metals such as copper (Cu), titanium (Ti), molybdenum (Mo) and tungsten (W), and high melting point metal silicides such as titanium silicide (TiSi), molybdenum silicide (MoSi) and tungsten silicide (WSi).

The read transistors 22 are provided at the respective pixels 12a, 12b on the surface of the wiring part 14, which is on the side of the 1st photoelectric conversion part 15. The read transistor 22 controls the movement of the charges stored in the photodiode 23a, 23b.

The 1st photoelectric conversion section 15 is provided between and adjacent to the wiring part 14 and the 2nd photoelectric conversion part 16. The 1st photoelectric conversion part 15 includes the photodiode 23a, 23b, the transparent insulating layer 24, the contact plug 25 and the storage diode 26.

The photodiodes 23a, 23b are provided in the p-type single crystal Si substrate 27 so as to correspond to the pixels 12a, 12b arranged in an array. The photodiodes 23a, 23b absorb a light of a wavelength range of one color of the three primary light colors and goes through the photoelectric conversion layer 6 described below, and perform photoelectric conversion.

Herein, the "three primary light colors" refer three colors of "a blue color", "a green color" and "a red color". The wavelength range of a blue light (a light of the blue wavelength range) is for example 400 to 500 nm, the wavelength range of a green light (a light of the green wavelength range) is for example 500 to 600 nm, and the wavelength range of a red light (a light of the red wavelength range) is for example 600 to 700 nm.

Examples of the photodiodes 23a, 23b include the n-type impurity diffusion region 28 provided in the p-type single crystal Si substrate 27. The PN junction surface is formed between the p-type single crystal Si substrate 27 and the n-type impurity diffusion region 28. Herein, the photodiodes 23a, 23b are not limited to the n-type impurity diffusion region provided in the p-type single crystal Si substrate, and can be a p-type impurity diffusion region provided in an n-type single crystal Si substrate.

The p-type single crystal Si substrate 27 is provided between and adjacent to the wiring part 14 and the transparent insulating layer 24. Usable examples of the p-type single crystal Si substrate 27 include Si in which a p-type impurity such as boron has been doped. Also, examples of the n-type impurity diffusion region 28 include Si in which a n-type impurity such as phosphorus has been doped.

The transparent insulating layer 24 is provided between and adjacent to the p-type single crystal Si substrate 27 and the 2nd photoelectric conversion part 16. The transparent insulation layer 24 is optically transmissive and insulates the photoelectric conversion layer 6 and the p-type single crystal Si substrate 27. Examples of the transparent insulating layer 24 include a $SiO_2$ film.

The contact plug 25 is provided so as to penetrate through the p-type single crystal Si substrate 27, and electrically connects the wiring part 14 and the 2nd photoelectric conversion part 16. Also, the contact plugs 25 are arranged at the respective pixels 12a, 12b so as to be positioned in a region surrounded on all four sides by the photodiodes 23a, 23b.

The contact plug 25 is electrically connected to the lower transparent electrode 33 and the storage diode 26, and can send the charges collected in the lower transparent electrode 33 to the storage diode 26. The contact plug 25 is covered with the insulating film 29. The material of the contact plug 25 is not particularly limited as long as it is an electroconductive material. Specific examples thereof include Si. Also, the insulating film 29 is not particularly limited as long as it is an insulating material. Specific examples thereof include a silicon nitride (SiN) film.

The storage diode 26 is provided at the end of the contact plug 25 which is on the side of the wiring part 14. The storage diode 26 temporarily stores the charges collected in the lower transparent electrode 33. A floating diffusion (not illustrated) is provided in the p-type single crystal Si substrate 27. The stored charges are sent from the storage diode 26 to the floating diffusion (not illustrated), and are converted into electric signals.

The 2nd photoelectric conversion part 16 is provided between and adjacent to the 1st photoelectric conversion part 15 and the color filter part 17. The 2nd photoelectric conversion part 16 include the lower transparent electrode 33, the planarization layer 34, the electron-blocking layer 5, the photoelectric conversion layer 6, the hole-blocking layer 7 and the upper transparent electrode 38.

In other words, the 2nd photoelectric conversion part 16 corresponds to the aforementioned organic photoelectric conversion device 1 except that the substrate 2 is omitted. Also, the anode 3 of the organic photoelectric conversion device 1 corresponds to the lower transparent electrode 33 of the 2nd photoelectric conversion section 16, and the cathode 8 of the organic photoelectric conversion device 1 corresponds to the upper transparent electrode 38 of the 2nd photoelectric conversion section 16. Therefore, the descriptions for the corresponding parts are omitted in this specification.

The lower transparent electrodes 33 are provided at the respective pixels 12a, 12b on the surface of the transparent insulating layer 24 which is on the side of the light receiving surface 11a. Also, the peripheral part of the projection area formed by projecting the lower transparent electrode 33 to the p-type single crystal Si substrate 27 overlaps the light receiving surfaces of the photodiodes 23a, 23b in a plan view. Examples of the material of the lower transparent electrode 33 include a transparent conductive material such as indium tin oxide (ITO).

The planarization layer 34 is provided between and adjacent to the photoelectric conversion layer 6 described below, and the lower transparent electrode 33 and the transparent insulating layer 24. The planarization layer 34 can planarize the uneven surfaces of the lower transparent electrode 33 and the transparent insulating layer 24. Examples of the material of the planarization layer 34 include the same materials as the planarization layer 4 of the aforementioned organic photoelectric conversion device 1.

The upper transparent electrode 38 is provided on the surface of the photoelectric conversion layer 6, which is on the side of the light receiving surface 11a, as a single sheet so as to cover a plurality of the photodiodes 23a, 23b. Because of the upper transparent electrode 38, it is possible to apply a bias voltage supplied from the outside to the photoelectric conversion layer 6.

When applying a bias voltage, the upper transparent electrode 38 can collect the charges generated in the photoelectric conversion layer 6 in the respective lower transparent electrodes 33. Examples of the material of the upper transparent electrode 38 include a transparent conductive material such as indium tin oxide (ITO).

The color filter part 17 is provided between and adjacent to the 2nd photoelectric conversion part 16 and the micro-lens 18. The color filter unit 17 includes the inorganic protective film 41, the planarization layer 42, and pluralities of the 1st color filter 43a and the 2nd color filter 43b.

The inorganic protective film 41 is provided on the surface of the upper transparent electrode 38, which is on the side of the light receiving surface 11a, as a single sheet. Examples of the inorganic protective film 41 include an aluminum oxide ($Al_2O_3$) film.

The planarization layer 42 is provided between and adjacent to the 2nd photoelectric conversion section 16 and the microlens 18. Examples of the material of the planarization layer 42 include silicon dioxide.

The pluralities of the 1st color filter 43a and the 2nd color filter 43b are provided in the planarization layer 42 so as to face the photodiodes 23a, 23b. The 1st color filter 43a absorbs a light of a specific wavelength range and is transmissive to a light of other wavelength ranges. Also, the 2nd color filter 43b can be the same as the first color filter 43a, and can be a different color filter which absorbs a light of other wavelength ranges.

For example, the 1st color filter 43a can be configured to absorb a blue light and to be transmissive to a green light and a red light, and the 2nd color filter 43b can be configured to absorb a green light and to be transmissive to a blue light and a red light.

By appropriately selecting the wavelength ranges of lights absorbed by the 1st color filter 43a and the 2nd color filter 43b, it is possible to select the wavelength range of a light absorbed by the photoelectric conversion layer 6.

The microlenses 18 are provided on the side of the light receiving surface 11a of the color filter portion 17 and at the positions which face the photodiodes 23a, 23b. For example, the microlens 18 can be a lens which forms a circle in planer view such that incident light is focused by the microlens 18. The optical centers of the respective microlenses 18 are positioned at the centers of the light receiving surfaces of the respective photodiodes 23a, 23b. The plan-view area of the microlens 18 is larger than the area of the light receiving surface of the photodiodes 23a, 23b.

Next, the production method for the solid-state imaging device 11 of the embodiment is described with reference to FIG. 3 to FIG. 11. FIG. 3 to FIG. 11 are the schematic diagrams representing the production method for the solid-state imaging device 11 of the embodiment.

Figure 3:
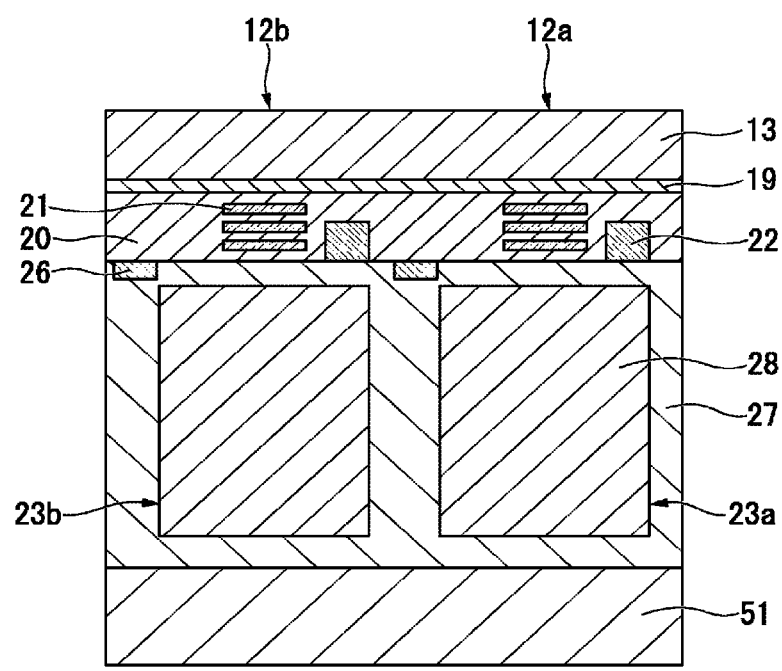
FIG. 3 is a schematic diagram representing the production method for the solid-state imaging device of the embodiment.

First, as shown in FIG. 3, the p-type single crystal Si substrate 27 is formed by epitaxially growing the Si layer, in which a p-type impurity such as boron has been doped, on the semiconductor substrate 51 such as a Si wafer.

Next, the respective pixels 12a, 12b within the p-type single crystal Si substrate 27 are subjected for example to the ion-implantation using an n-type impurity such as phosphorus and an annealing treatment, to thereby form the n-type impurity diffusion region 28 within the p-type single crystal Si substrate 27. Through this process, the photodiodes 23a, 23b are formed in the solid-state imaging device 11 by the PN junction between the p-type single crystal Si substrate 27 and the n-type impurity diffusion region 28.

Next, the inner surface of the p-type single crystal Si substrate 27 is subjected for example to the ion-implantation using an n-type impurity such as phosphorus and an annealing treatment, to thereby form the other n-type impurity diffusion region such as the storage diode 26. If necessary, it is possible to form the pixel isolation region, etc. (not illustrated) by further subjecting the inner surface of the p-type single crystal Si substrate 27 to the ion-implantation using an p-type impurity such as boron and an annealing treatment.

Next, the insulating layer 20 is formed on the p-type single crystal Si substrate 27 together with the multilayer wiring 21 and the read transistor 22. Specifically, the read transistor 22, etc. is formed on the upper surface of the p-type single crystal Si substrate 27, followed by repeating the step of forming the Si oxide layer, the step of forming a predetermined wiring pattern on the Si oxide layer, and the step of embedding Cu, etc. within the wiring pattern. This process forms the insulating layer 20 provided with the multilayer wiring 21 and the read transistor 22, etc.

Next, an adhesive is applied onto the upper surface of the insulating layer 20, to thereby form the adhesive layer 19. Then, the supporting substrate 13 such as a Si wafer is attached onto the upper surface of the adhesive layer 19. Herein, the attachment of the insulating layer 20 and the supporting substrate 13 is not limited to the attachment using an adhesive, but the direct attachment of the insulating layer 20 and the supporting substrate 13 is also possible by subjecting the insulating layer 20 to the polishing such as CMP (Chemical Mechanical Polishing) so as to prepare a flat and smooth surface thereof.

Figure 4:
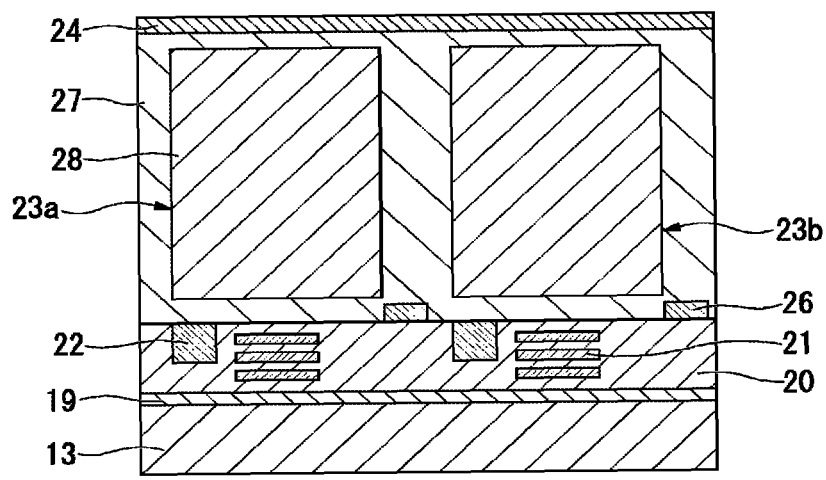
FIG. 4 is a schematic diagram representing the production method for the solid-state imaging device of the embodiment.

Next, the surface of the Si wafer including the photodiodes 23a, 23b, which is on the opposite side to the supporting substrate 13, is ground by a grinding apparatus such as a grinder, to thereby reduce the thickness of the Si wafer to a predetermined thickness. Then, the surface of the semiconductor substrate is polished by a polishing apparatus such as a CMP apparatus, and moreover, is subjected to wet etching, etc., to thereby remove the damaged layer of the surface of the semiconductor substrate. This process exposes the light-receiving surface of the p-type single crystal Si substrate 27 as shown in FIG. 4. Thereafter, the transparent insulating layer 24 made of a transparent insulating material such as $SiO_2$ is formed on the upper surface of the p-type single crystal Si substrate 27.

Figure 5:
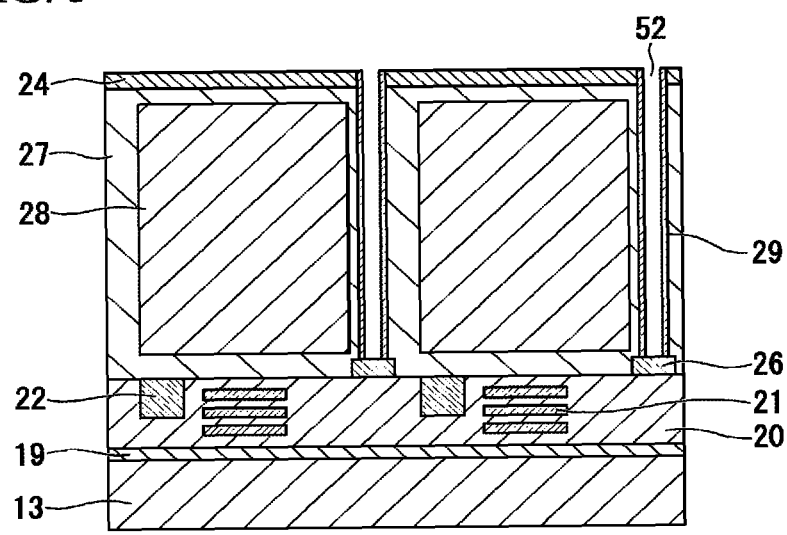
FIG. 5 is a schematic diagram representing the production method for the solid-state imaging device of the embodiment.

Next, as shown in FIG. 5, the transparent insulating layer 24 and the p-type single crystal Si substrate 27 at the positions surrounded on all four sides by the respective photodiodes are removed by RIE (Reactive Ion Etching), etc. until reaching the top of the storage diode 26. This process forms the trenches 52. On the inner surface of the trench 52, the insulating film 29 made of an insulating material such as SiN is formed by a CVD (Chemical Vapor Deposition) method, etc.

Figure 6:
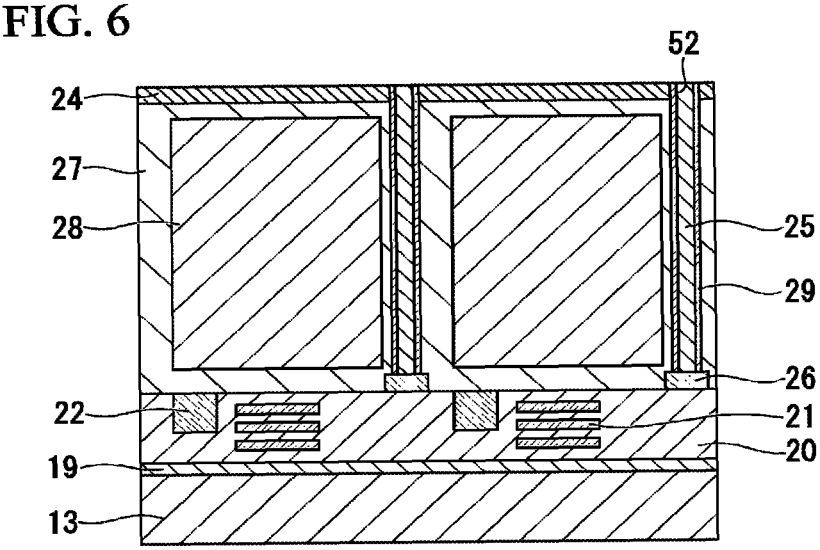
FIG. 6 is a schematic diagram representing the production method for the solid-state imaging device of the embodiment.

Next, as shown in FIG. 6, within the trenches 52 having the inner surface coated with the insulating film 29, the contact plugs 25 formed of an electroconductive material such as Si are embedded by a CVD method, etc. Herein, the embedding method of the contact plug 25 is not limited to the aforementioned method. Before and after the step of forming the impurity diffusion region such as the storage diode 26, it is possible to form the other n-type impurity diffusion region as the contact plug 25 by subjecting the inner surface of the p-type single crystal Si substrate 27 to the ion-implantation using an n-type impurity such as phosphorus and an annealing treatment.

Figure 7:
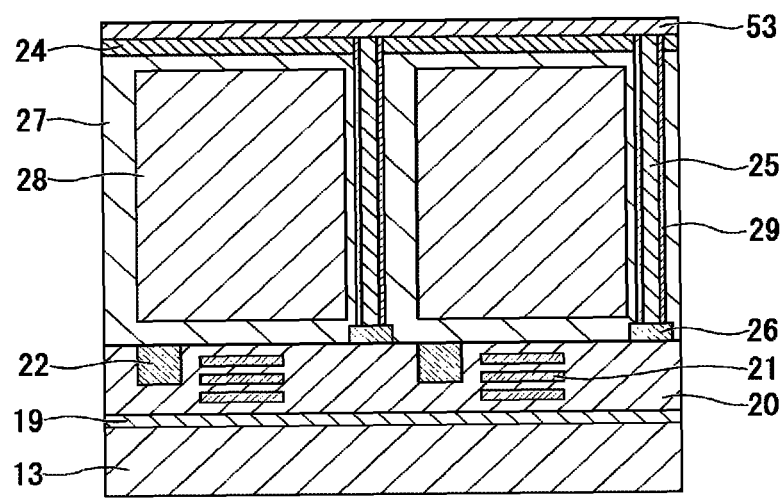
FIG. 7 is a schematic diagram representing the production method for the solid-state imaging device of the embodiment.

Next, as shown in FIG. 7, the electroconductive layer 53 made of a transparent conductive material such as ITO is formed on the upper surface of the transparent insulating layer 24 and the upper surfaces of the exposed contact plugs 25.

Figure 8:
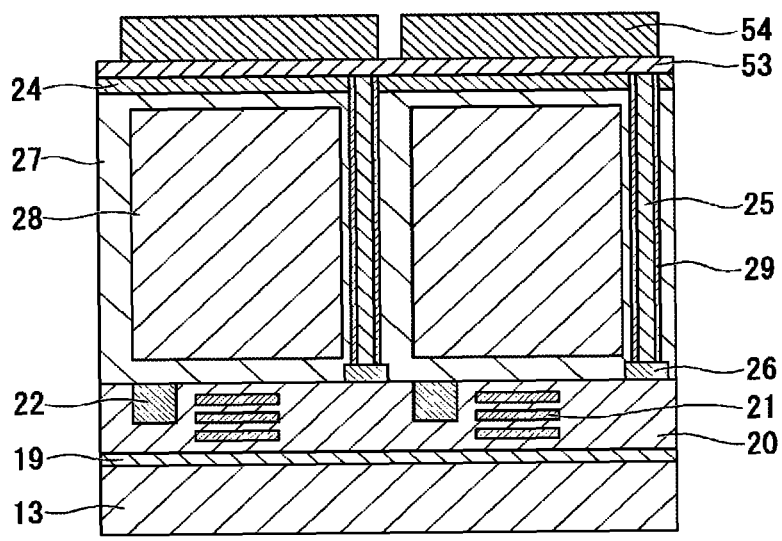
FIG. 8 is a schematic diagram representing the production method for the solid-state imaging device of the embodiment.
Figure 9:
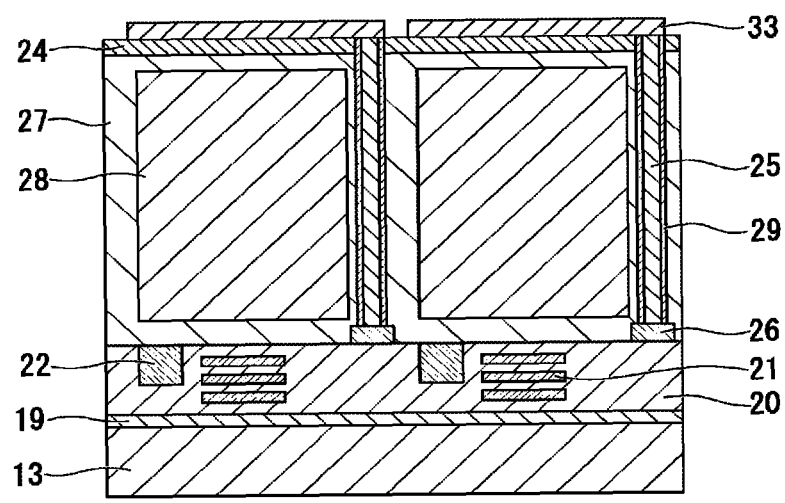
FIG. 9 is a schematic diagram representing the production method for the solid-state imaging device of the embodiment.

Next, as shown in FIG. 8, a resist, etc. is applied on the upper surface of the electroconductive layer 53, and then, photolithography is used to remove the resist other than the resist at the part of the formation position for the lower transparent electrode 33. The remaining resist 54 is used as a mask, and the electroconductive layer of the part uncovered with the resist is removed by ME, etc., to thereby form the lower transparent electrode 33 as shown in FIG. 9. Thereafter, the resist 54 used as a mask is removed.

Figure 10:
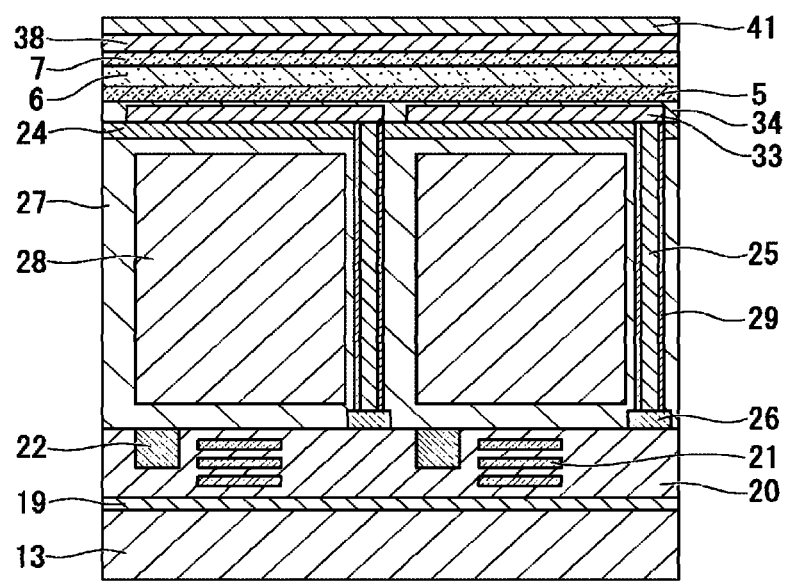
FIG. 10 is a schematic diagram representing the production method for the solid-state imaging device of the embodiment.

Next, as shown in FIG. 10, a transparent resin is applied on the lower transparent electrode 33 and the transparent insulating layer 24 by a coating process such as a spin coating method. Through this process, it is possible to form the planarization layer 34. Thereafter, a film made of TPD (N,N'-diphenyl-N,N'-di(m-tolyl)benzidine), etc. is formed on the upper surface of the planarization layer 34 by a vacuum deposition method, to thereby form the electron-blocking layer 5.

Next, on the upper surface of the electron-blocking layer 5, the photoelectric conversion layer 6 is formed by a vacuum deposition method, etc. Specifically, the photoelectric conversion layer 6 can be formed by depositing a material that selectively absorbs a light of a desired wavelength range or by selecting a plurality of materials that selectively absorb lights of different wavelength ranges and simultaneously depositing the plurality of materials. Thereafter, a film made of F201, etc. is formed on the upper layer of the photoelectric conversion layer 6 by a vacuum deposition method, etc., to thereby form the hole-blocking layer 7.

Figure 11:
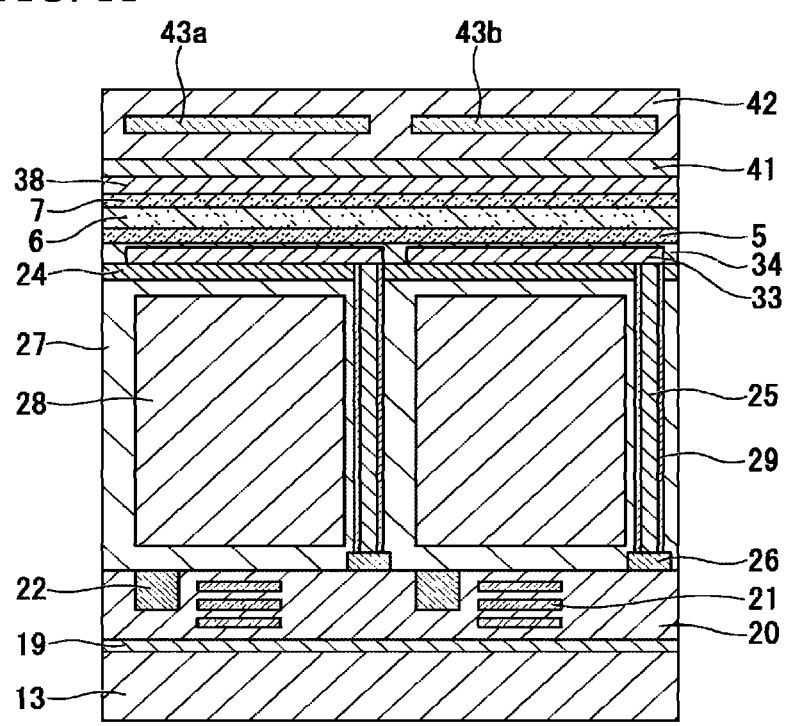
FIG. 11 is a schematic diagram representing the production method for the solid-state imaging device of the embodiment.

Next, on the upper surface of the hole-blocking layer 7, the upper transparent electrode 38 made of a transparent electroconductive material such as ITO is formed by a sputtering method, etc. Thereafter, on the upper surface of the upper transparent electrode 38, an $Al_2O_3$ film is formed as the inorganic protective film 41 by a sputtering method, etc. Thereafter, on the inorganic protective film 41, the planarization layer 42 made of a transparent resin is formed as shown in FIG. 11.

Next, the 1st and 2nd color filters 43a, 43b are formed at the positions, which respectively face the light-receiving surfaces of the respective photodiodes 23a, 23b in the planarization layer 42, by photolithography using a pigment or a dye for color filters which are transmissive to a green light and a red light. Then, the planarization layer 42 made of a transparent resin is further formed so as to cover the 1st and 2nd color filters 43a, 43b. Through this process, the 1st and 2nd color filters 43a, 43b are embedded in the planarization layer 42.

Finally, the microlenses 18 made of an acrylic organic compound, etc. are formed on the upper surface of the planarization layer 42 and at the positions, which respectively face the light-receiving surfaces of the respective photodiodes 23a, 23b, in a size to cover the light receiving surfaces in planer view. Through the aforementioned process, the solid-state imaging device 11 of the embodiment is produced.

In the aforementioned embodiment, the solid-state image device 11 includes the planarization layer 4 and the electron-blocking layer 5, but can be free from any one or both of the planarization layer 4 and the electron-blocking layer 5.

According to the embodiment described above, the solid-state imaging device 11 includes the compound represented by the aforementioned general formula (1) or the aforementioned formula (2). Therefore, it is possible to achieve high photoelectric conversion efficiency and a low dark current.

Figure 12:
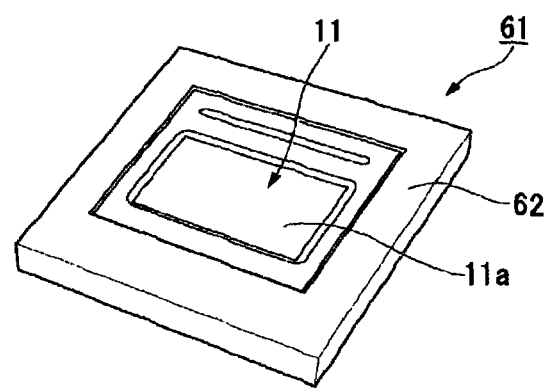
FIG. 12 is a perspective view showing an example of the CMOS image sensor using the solid-state imaging device of the embodiment.

FIG. 12 is a perspective view showing an example of the CMOS image sensor 61 using the solid-state imaging device 11 of the embodiment. The CMOS image sensor 61 is a CMOS image sensor of Full HD (1080p) type. The CMOS image sensor 61 includes the solid-state imaging device 11 and the mold resin 62.

The mold resin 62 is provided so as to cover the part other than the light receiving surface 11a of the solid-state imaging device 11. By integrating the solid-state imaging device 11 and the mold resin 62, it is possible to protect the solid-state imaging device 11 from external stress, moisture and contaminants.

The CMOS image sensor 61 is used in various mobile terminals such as a digital camera and a cellular phone (including a smartphone), a security camera, and an imaging device such as a web camera using the Internet.

Figure 13:
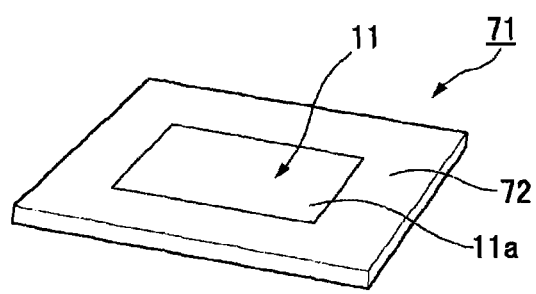
FIG. 13 is a perspective view showing another example of the CMOS image sensor using the solid-state imaging device of the embodiment.

FIG. 13 is a perspective view showing another example of the CMOS image sensor using the solid-state imaging device 11 of the embodiment. The CMOS image sensor 71 is a CMOS image sensor of VGA type. The CMOS image sensor 71 includes the solid-state imaging device 11 and the mold resin 72.

The mold resin 72 is provided so as to cover the part other than the light receiving surface 11a of the solid-state imaging device 11. By integrating the solid-state imaging device 11 and the mold resin 72, it is possible to protect the solid-state imaging device 11 from external stress, moisture and contaminants.

The CMOS image sensor 71 is used in various mobile terminals such as a digital camera and a cellular phone (including a smart phone), a security camera, and an imaging device such as a web camera using the Internet.

Figure 14:
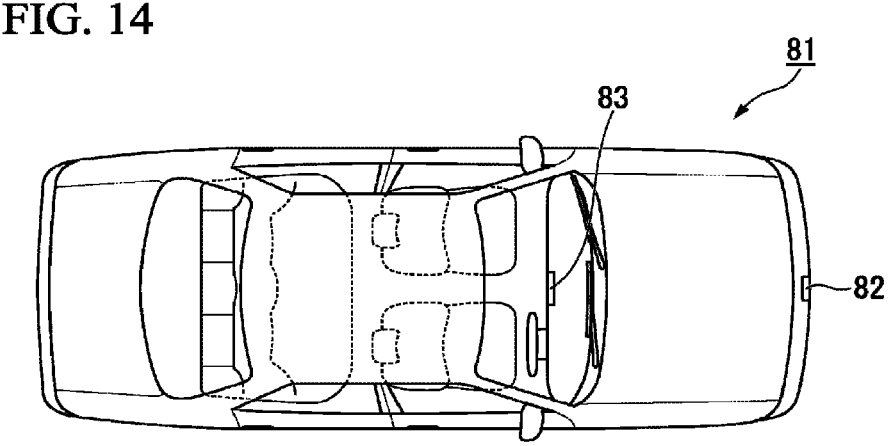
FIG. 14 is a plan view showing an example of the vehicle including the camera equipped with the CMOS image sensor.

FIG. 14 is a plan view showing an example of the vehicle 81 including the camera 82 equipped with the aforementioned CMOS image sensor 61 or CMOS image sensor 71. The vehicle 81 includes the camera 82 and the display 83. The camera 82 is provided at the forward end of the vehicle 81, and it is possible to shoot the front of the vehicle 81. Also, the display 83 is provided in the front of the driver's seat of the vehicle 81, and it is possible to show the images shot by the camera 82. By checking the images shot by the camera 82 on the display 83, it is possible to check blind spots during parking, etc.

Figure 15:
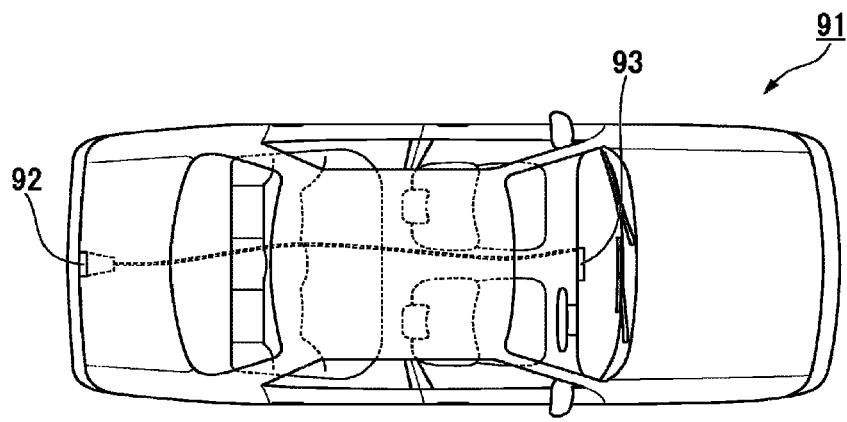
FIG. 15 is a plan view showing another example of the vehicle including the camera equipped with the CMOS image sensor.

FIG. 15 is a plan view showing another example of the vehicle 91 including the camera 92 equipped with the aforementioned CMOS image sensor 61 or CMOS image sensor 71. The vehicle 91 includes the camera 92 and the display 93. The camera 92 is provided at the back end of the vehicle 91, and it is possible to shoot the back of the vehicle 91. Also, the display 93 is provided in the front of the driver's seat of the vehicle 91, and it is possible to show the images shot by the camera 92. By checking the images shot by the camera 92 on the display 93, it is possible to check the back.

Figure 16:
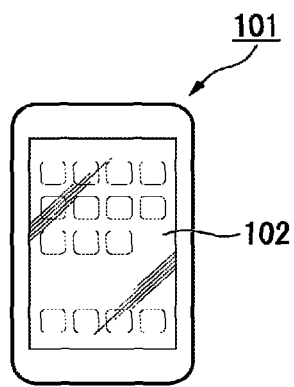
FIG. 16 is a plan view showing the smartphone including the camera equipped with the CMOS image sensor.

FIG. 16 is a plan view showing the smartphone 101 including the camera equipped with the aforementioned CMOS image sensor 61 or CMOS image sensor 71. The smartphone 101 includes a camera (not illustrated) and the touch panel 102. When a camera is provided at the front upper part of the smartphone 101, it is possible to shoot the front of the smartphone 101. Also, the touch panel 102 is provided in the center of the front of the smartphone, and it is possible to show the images shot by a camera.

Figure 17:
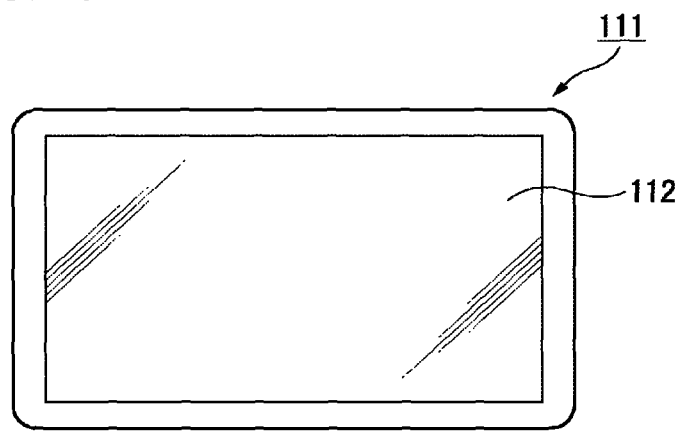
FIG. 17 is a plan view showing the tablet including the camera equipped with the CMOS image sensor.

FIG. 17 is a plan view showing the tablet 111 including the camera equipped with the aforementioned CMOS image sensor 61 or CMOS image sensor 71. The tablet 111 includes a camera (not illustrated) and the touch panel 112. When a camera is provided at the front upper part of the tablet 111, it is possible to shoot the front of the tablet 111. Also, the touch panel 112 is provided in the center of the front of the tablet, and it is possible to show the images shot by a camera.

EXAMPLES

Hereinafter, Example 1 is described.

The compound of Example 1 was synthesized by the same method as the synthesis method for the compound of the aforementioned embodiment.

The compound of Example 1 was synthesized under the following conditions.

First, under a nitrogen atmosphere, N-phenyl-O-phenylenediamine (5.7 g, 30.9 mmol) was dissolved in N-methylpyrrolidone (NMP) (23 ml). Thereafter, the NPOP solution is cooled to 10° C., 4-bromobenzoyl chloride (4BC) (6.8 g, 30.9 mmol) was dissolved in NMP (3 ml), and this 4BC solution was added dropwise in the NPOP solution. Thereafter, the reaction solution was stirred at room temperature for 1 hour. Thereafter, water (50 ml) was added dropwise therein, to thereby terminate the reaction, and the reaction solution was extracted with ethyl acetate (100 ml). Thereafter, the organic layer was washed with a saturated saline solution, and was dried over anhydrous sodium sulfate. Thereafter, the organic layer was concentrated under a reduced pressure, to thereby obtain the compound represented by the aforementioned formula (3).

Next, under a nitrogen atmosphere, xylene (100 ml) was added to the compound represented by the formula (3) (9.9 g, 27.0 mmol) and p-toluene sulfonic acid (1.5 g), and the reaction solution was heated to 130° C. and refluxed to be dehydrated for 5 hours. Thereafter, the reaction solution was cooled to room temperature, and was filtrated to obtain the solid product. This solid product was dissolved again in chloroform (200 ml), and the chloroform solution was washed with a saturated sodium bicarbonate aqueous solution and water. On the other hand, ethyl acetate (50 ml) was added to the xylene-soluble part which was the filtrate obtained by the filtration, and then, this mixed solution was washed with a saturated sodium bicarbonate aqueous solution and water in the same manner as described above. Thereafter, the organic layers were mixed, and the mixed solution was dried over anhydrous sodium sulfate. Thereafter, the mixed solution was concentrated under a reduced pressure, to thereby obtain a crude product. This crude product was purified through column purification, to thereby obtain the compound represented by the aforementioned formula (4) (8.1 g, 23.2 mmol).

Next, under a nitrogen atmosphere, magnesium (2.9 g, 120 mmol), tetrahydrofuran (THE) (210 ml) and a small amount of iodine were added in a reactor, and the compound represented by the aforementioned formula (5) (30 g, 120 mmol) was added dropwise therein at an internal temperature of 20° C. or less. Thereafter, the reaction solution was stirred for 1 hour while maintaining an internal temperature of 20° C. or less. Then, the compound represented by the following formula (6) (14.5 g, 50 mmol) was added therein, and the reaction solution was further stirred overnight. Thereafter, hydrochloric acid (2 N, 140 ml) was added dropwise therein, to thereby terminate the reaction, and the reaction solution was extracted with ethyl acetate (200 ml). Thereafter, the extracted solution was washed with a saturated saline solution and water. Then, anhydrous magnesium sulfate was added therein, and the solution was stirred for 1 hour. Thereafter, the solution was filtrated, and the obtained filtrate was concentrated under a reduced pressure, to thereby obtain the compound represented by the following formula (7) (28.5 g).

Next, the compound represented by the formula (7) (28.5 g, 45.7 mmol) was added in the acetic acid (300 ml) and dissolved at 50° C. Thereafter, tin (II) chloride dihydrate (20 g, 88.6 mmol) was added therein and stirred at 80° C. for 2 hours. Thereafter, the reaction solution was cooled, and was added into water (300 ml), followed by filtration to obtain the solid product. Thereafter, ethyl acetate (250 ml) was added to this solid product so as to dissolve the solid product, and the obtained solution was washed with a saturated sodium bicarbonate aqueous solution and water. Thereafter, the anhydrous sodium sulfate was added therein, and the solution was stirred. One hour later, the solution was filtrated, and the obtained filtrate was concentrated under a reduced pressure, to thereby obtain the compound represented by the following formula (8) (12.4 g, 21 mmol).

Next, under a nitrogen atmosphere, the compound represented by the formula (8) (7.1 g, 12 mmol) and the compound represented by the following formula (9) (3.1 g, 12 mmol) were added and dissolved in 1,4-dioxane (150 ml). Thereafter, potassium acetate (3.5 g, 36 mmol) and Pd(dppf).$CH_2Cl_2$ (0.3 g) were added therein, and the reaction solution was stirred for 2 hours at 80° C. Thereafter, the reaction solution was cooled to room temperature and dispersed in water (IL), and the precipitated solid product was collected by filtration. The obtained solid product was dissolved in chloroform (300 ml), and anhydrous sodium sulfate and activated clay were added therein, followed by stirring for 1 hour. Thereafter, the solution was filtrated, and the obtained filtrate was concentrated under a reduced pressure, to thereby obtain the compound represented by the following formula (10) (6.5 g, 10.2 mmol).

Next, under a nitrogen atmosphere, the compound represented by the formula (4) (3.6 g, 10.2 mmol) and the compound represented by the formula (10) (6.5 g, 10.2 mmol) were added and dissolved in xylene (150 ml) and 1,4-dioxane (65 ml). Thereafter, the sodium carbonate aqueous solution (2 N, 40 g) and tetrakis(triphenylphosphine) palladium (40 g) were added thereto, and the reaction solution was stirred at 80° C. overnight. Thereafter, the reaction solution was cooled to room temperature, and chloroform (500 ml) was added therein. The reaction solution was separated into two layers, and the collected organic layer was washed with water. Thereafter, anhydrous sodium sulfate and activated clay were added in the organic layer, and the organic layer was stirred for 1 hour. Thereafter, the organic layer was filtrated, and xylene and chloroform were removed from the obtained filtrate by the concentration under a reduced pressure, to thereby obtain the crude product. This crude product was purified by silica gel column chromatography, and the purified product was dried under a reduced pressure at 45° C. Through these processes, F201 was obtained.

Next, the HOMO level and the LUMO level of the synthesized F201 were measured. The HOMO level and the LUMO level of LG201 represented by the following formula (11) were also measured by way of comparison. Herein, the measurements of the HOMO level and the LUMO level were carried out by the calculation using Gaussian (a DFT Method in which B3LYP was used, and the basis function was 6-31G*).

[Chemical Formula 11]

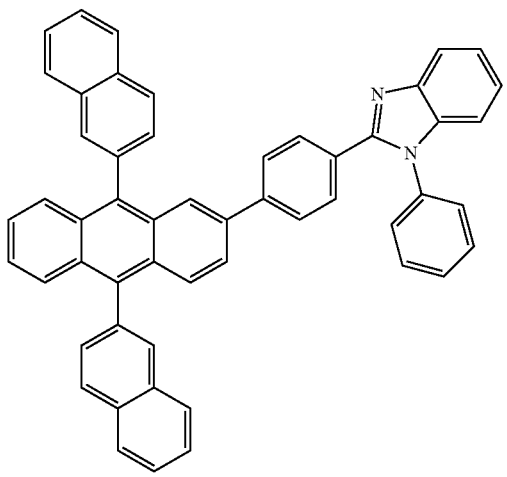

(11)

The HOMO level of F201 was 5.6 eV, and the LUMO level of F201 was 2.4 eV. On the other hand, the HOMO level of LG201 was 5.1 eV, and the LUMO level of LG201 was 1.8 eV. From the above results, it could be confirmed that F201 had the deeper HOMO level and LUMO level than LG201.

Hereinafter, Example 2 is described.

The organic photoelectric conversion device of Example 2 was produced to have the same configuration as the organic photoelectric conversion device 1 of the embodiment described above. In other words, the organic photoelectric conversion device of Example 2 included the anode, the planarization layer, the electron-blocking layer, the photoelectric conversion layer, the hole-blocking layer and the cathode, which were laminated in this order.

Herein, F201 was used as the material of the hole-blocking layer.

Regarding the thicknesses of the respective layers in the organic photoelectric conversion device of Example 2, the anode had the thickness of 50 nm, the planarization layer had the thickness of 35 nm, the electron-blocking layer had the thickness of 3 nm, the photoelectric conversion layer had the thickness of 80 nm, the hole-blocking layer had the thickness of 6 nm, and the cathode had the thickness of 150 nm.

Hereinafter, Example 3 is described.

The organic photoelectric conversion device of Example 3 had the same configuration as the organic photoelectric conversion device of Example 2 except that the thickness of the hole-blocking layer in the organic photoelectric conversion device of Example 2 was 3 nm.

Hereinafter, Comparative Example 1 is described.

The organic photoelectric conversion device of Comparative Example 1 had the same configuration as the organic photoelectric conversion device of Example 2 except that the hole-blocking layer of the organic photoelectric conversion device of Example 2 was omitted and the photoelectric conversion layer and the cathode were laminated adjacent to each other.

The aforementioned organic photoelectric conversion devices of Example 2, Example 3 and Comparative Example 1 were subjected to the measurements for the external quantum efficiency (EQE) and a dark current. Herein, the measurements for EQE and a dark current were measured by a spectral sensitivity measurement apparatus (manufactured by Bunkoukeiki Co., Ltd., trade name: "CEP-V25ML"). The wavelength of the irradiation light used for the measurements was 530 nm, and the power thereof was 50 μW/cm$^2$.

When applying the voltage of −5 V, the EQE values were 73.57% in Example 2, 71.12% in Example 3 and 70.30% in Comparative Example 1, and the EQE value was increased by using F201 as the hole-blocking layer. Also, when applying the voltage of −5 V, the dark current densities were 1.10×10$^{-10}$ A/cm$^2$ in Example 2 and 1.43×10$^{-10}$ A/cm$^2$ in Example 3 and 2.41×10$^{-10}$ A/cm$^2$ in Comparative Example 1, and the dark current density was decreased by using the F201 as the hole-blocking layer.

From the aforementioned results, by using F201 as the hole-blocking layer, it could be confirmed that it was possible to achieve high photoelectric conversion efficiency and a low dark current.

While certain embodiments have been described, these embodiments have been presented by way of example only, and are note intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A compound represented by the following general formula (1)

[Chemical Formula 1]

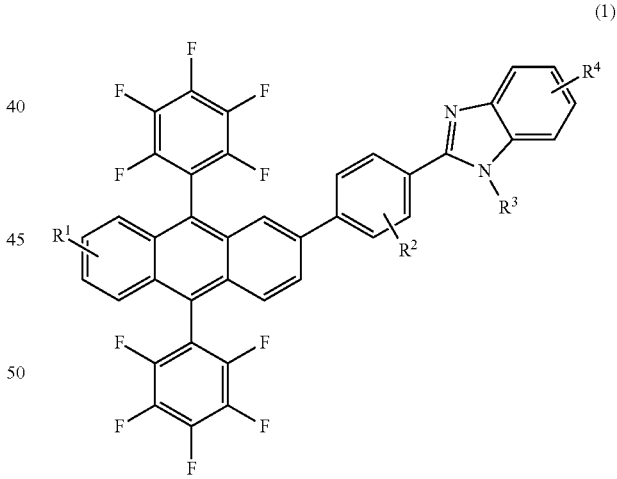

(1)

In the general formula (1), $R^1$ to $R^4$ respectively independently represent a hydrogen atom, a linear or branched alkyl group, a fluoroalkyl group, or an aryl group.

2. An organic photoelectric conversion devise comprising:
a photoelectric conversion layer which absorbs a light and performs photoelectric conversion; and
the compound according to claim 1, wherein
a layer containing the compound is laminated adjacent to the photoelectric conversion layer.

3. A solid-state imaging device comprising the organic photoelectric conversion devise according to claim 2.

4. A compound represented by the following formula (2)

[Chemical Formula 2]

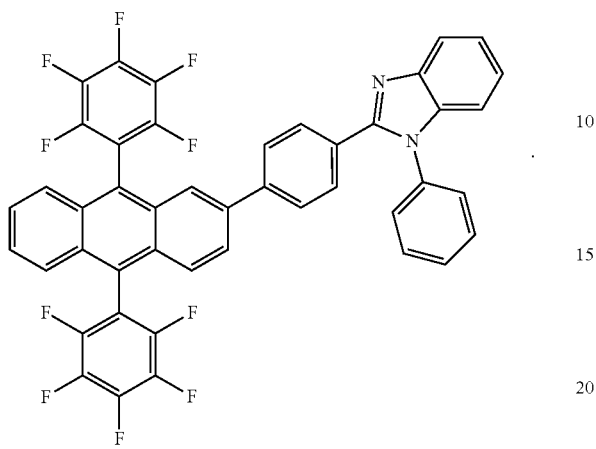

(2)

5. An organic photoelectric conversion devise comprising:
   a photoelectric conversion layer which absorbs a light and performs photoelectric conversion; and
   the compound according to claim 4, wherein
   a layer containing the compound is laminated adjacent to the photoelectric conversion layer.

6. A solid-state imaging device comprising the organic photoelectric conversion devise according to claim 5.

* * * * *